United States Patent [19]

Srinivasan et al.

[11] 3,973,567

[45] Aug. 10, 1976

[54] WRAPPED SANITARY NAPKINS

[75] Inventors: Subramanian Srinivasan; Fred H. Steiger, both of East Brunswick, N.J.

[73] Assignee: Personal Products Company, Milltown, N.J.

[22] Filed: May 19, 1975

[21] Appl. No.: 578,978

[52] U.S. Cl. ............................ 128/290 R; 128/284; 229/48 SB
[51] Int. Cl.² ................................................ A61F 13/16
[58] Field of Search ........ 128/284, 287, 262, 290 R, 128/156; 229/48 SB, 80, 87, 92.5, 92.7

[56] References Cited
UNITED STATES PATENTS

| | | | |
|---|---|---|---|
| 1,720,721 | 7/1929 | Culotta | 229/92.7 X |
| 3,024,788 | 3/1962 | Lane | 128/290 R X |
| 3,035,578 | 5/1962 | Elmore | 128/290 R |
| 3,193,181 | 7/1965 | Konjevich et al. | 229/87 |
| 3,230,956 | 1/1966 | Kargul | 128/290 R |
| 3,274,999 | 9/1966 | Robinson | 128/156 |
| 3,307,773 | 3/1967 | Kratzer et al. | 229/80 |
| 3,367,334 | 2/1968 | Testa | 128/290 R |
| 3,570,491 | 3/1971 | Sneider | 128/290 R |
| 3,604,423 | 9/1971 | Fraser | 128/290 R |
| 3,731,689 | 5/1973 | Schaar | 128/287 |

*Primary Examiner*—Aldrich F. Medbery
*Attorney, Agent, or Firm*—J. Lipow

[57] ABSTRACT

A sanitary napkin having an adhesive element thereon for attaching to a undergarment is provided with means for both protecting the napkin and the adhesive element prior to use and for disposing of the napkin after use. The means comprise providing the napkin with a wrapper sheet of flexible material overlying one major surface, and the sides of the napkin and at least partially overlapping on the second major surface of the napkin. The sheet is releasably adhered to and held in place by the adhesive element.

7 Claims, 14 Drawing Figures

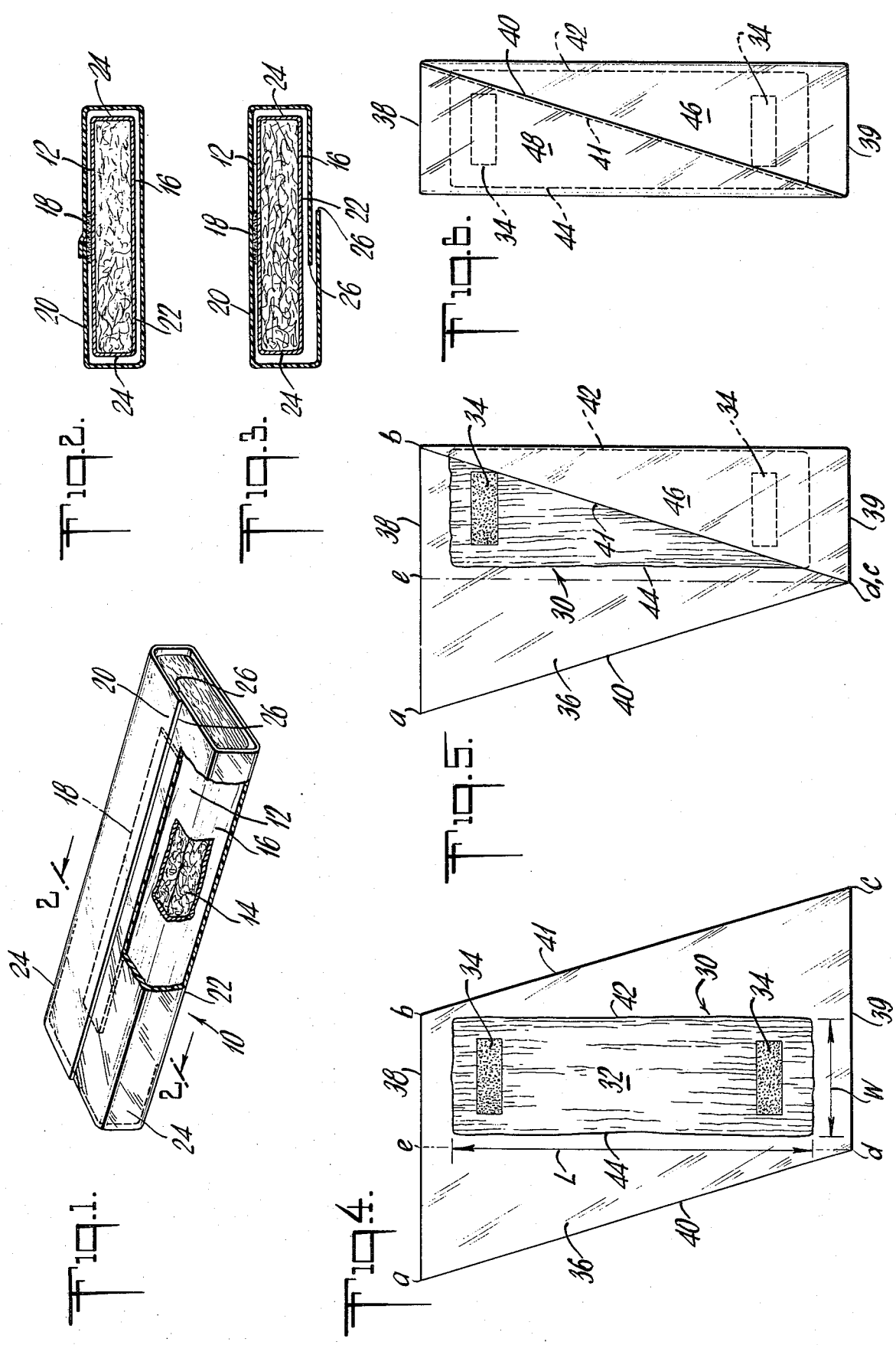

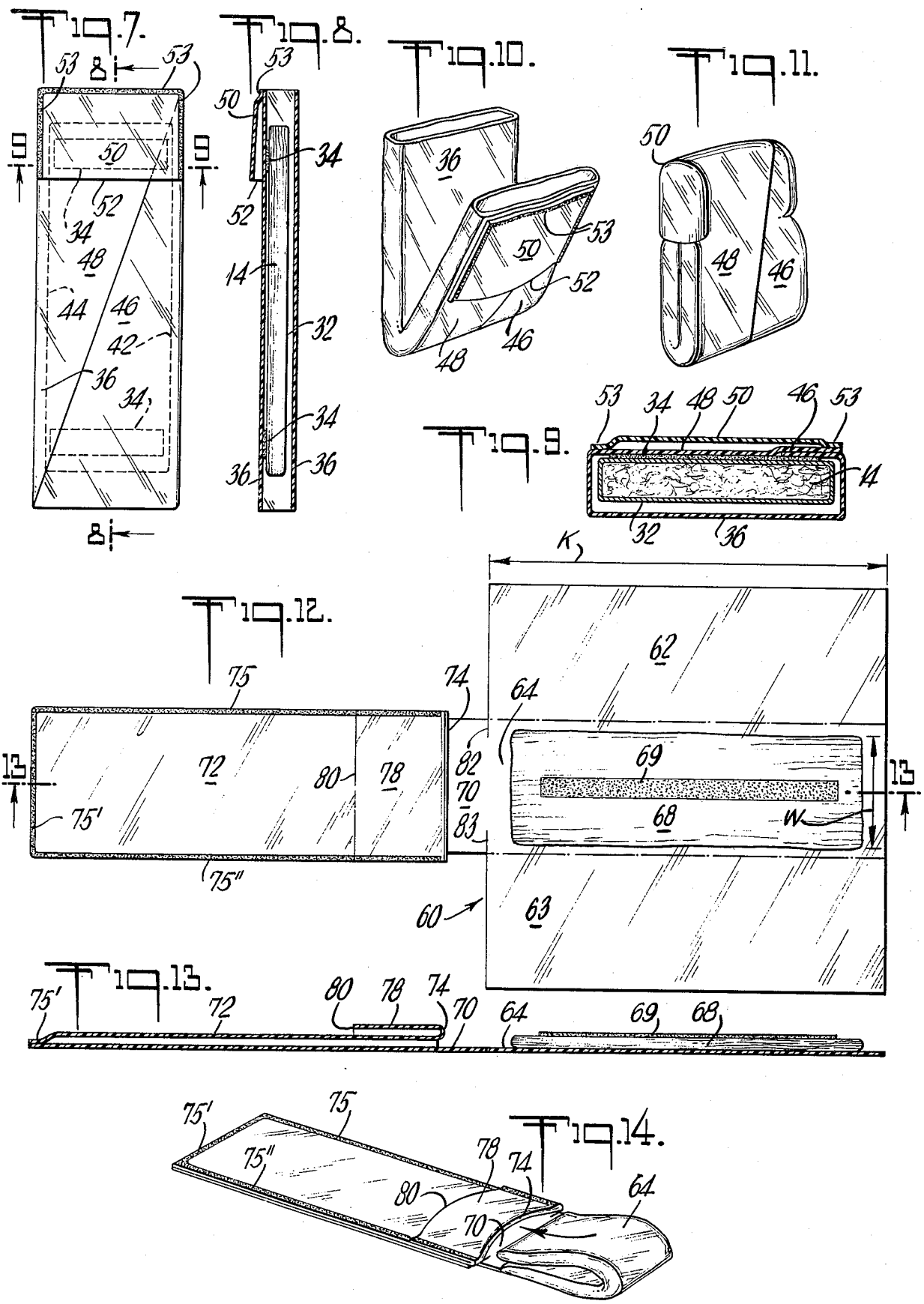

WRAPPED SANITARY NAPKINS

BACKGROUND OF THE INVENTION

This invention concerns the handling and disposing of sanitary napkins and, in particular, concerns means for protecting a sanitary napkin having an adhesive attachment system before use and means for disposing of such a napkin after use.

The art is now replete with suggestions for sanitary napkins which can be applied to the crotch portion of an undergarment and held in place there by an adhesive element thus eliminating the need for the more conventional attachment systems such as belts, pins, and the like. Generally, such napkins comprise an adhesive element in the form of a rectangular layer of pressure-sensitive adhesive or a double faced adhesive tape arranged in various patterns on the bottom surface of the napkin (i.e., the surface of the napkin worn away from the body). Because such adhesive elements are necessarily tacky, it is essential that a protective layer be provided to overlie the adhesive element prior to use, the protective layer being capable of releasably peeling from the adhesive element at the time of use. Such protective layers have heretofor comprised a relatively stiff sheet of material essentially co-extensive in size with the adhesive element and being specially treated so as to easily peel from the adhesive element at the time of use. For example, a heavy paper strip having one surface coated with silicone has been used commercially.

Napkins of this type are then typically packaged, without further protection, in cardboard, or flexible film packages of eight, 10, 12 or more napkins.

Several drawbacks are associated with the construction and packaging of adhesively attached napkins in the manner described above. Firstly, a large number of napkins packaged in a single package, necessarily means that the package will remain open, with the unused napkins exposed and subjected to soiling, for a period of days and even for as much as a month or longer. Secondly, a user will frequently remove several napkins from the large package and place them in her handbag for future use. The exposed napkins are once again subject to being soiled when carried in a purse. Thus, it is advantageous to individually wrap each napkin. Unfortunately, the additional materials and processing steps required to so wrap each napkin would appear to greatly increase the cost of the product to the consumer and heretofor, no economical means have thus far been suggested for accomplishing this without such increased cost.

Still another problem which relates to the above described napkins is in the disposal of the used napkin. Ideally a used napkin should be fully wrapped immediately after use and disposed of in a closed trash receptacle. Understandably however, there is a great reluctance toward any extensive handling of the used napkin and so all too frequently, the napkin is disposed of in an unwrapped condition or alternatively is simply flushed in a water closet where it often causes clogging of the associated piping. Several suggestions are found in the prior art for alleviating this problem and are exemplified by U.S. Pat. No. 2,750,033 issued June 12, 1956 to J. B. Pickens or U.S. Pat. No. 2,766,927, issued on Oct. 16, 1956 to J. S. Wallace. Each of these patents describe a closed envelope or receptacle for receiving a soiled napkin, the envelope being reclosable or sealable after receiving the same. While it appears that these suggestions would function quite well with conventional napkins, it is likewise apparent that these complex, specially designed receptacles would represent a substantial portion of the cost of the product to the consumer. Additionally, when attempting to use these receptacles with the newly developed adhesively attached napkins, it is exceedingly difficult to slide such a used napkin into an envelope-like receptacle without extensive handling of the soiled napkin. This is primarily due to the resistance to sliding caused by the now exposed adhesive element which is tacky and adheres to the walls of the envelope.

Accordingly, there is a need for an inexpensive, yet effective means for packaging and disposing of adhesively attached sanitary napkins.

SUMMARY OF THE INVENTION

In accordance with this instant invention, a sanitary napkin having an adhesive element thereon for attaching to an undergarment is provided with means for both protecting the napkin and the adhesive element prior to use and for disposing of the napkin after use. It has been discovered that such means may be provided without unduly increasing the cost of the napkin to the consumer, while still overcoming the problems associated with prior attempts to meet these desired results.

Specifically, the means of this invention comprise providing an adhesively attached napkin with a sheet of flexible material overlying one major surface and the sides of said napkin and at least partially overlapping on the second major surface of said napkin, said sheet being releasably adhered to and held in place by said adhesive element. Preferably, the sheet overlaps on that surface on which the adhesive element is disposed. Thus, by simply providing the overlapped sheet as described above, the napkin is protected from soiling and because the sheet overlies the adhesive element, the need for a protective, specially treated, release strip found to be necessary in prior art adhesively attached napkins is now completely eliminated. In fact, the adhesive element is utilized as the means for holding the flexible sheet in place, thus eliminating the need for special sealing steps in fabricating an envelope to protect the napkin. The provision of the simple sheet construction in combination with the utilization of the adhesive element to hold it in place represents only a small fraction of the cost of the finished product and this cost is offset by the savings realized in eliminating the release strip heretofore required.

In use, the sheet is simply unwrapped from the napkin and releases easily from the adhesive element leaving the napkin ready for use. The sheet may then be folded and placed in a handbag or another convenient place until the napkin is to be discarded. At this time, the sheet may be unfolded, the napkin laid onto the unfolded sheet and then wrapped in the sheet with the adhesive element again acting to hold the sheet in place. Thus, the now wrapped napkin may safely and sanitarily be disposed of in a trash receptacle.

In a preferred embodiment of the invention, the sheet is in the form of a parallelogram having both short parallel sides and long parallel sides. The short sides are at least twice as long as the width of the napkin and are spaced apart by a distance at least as long as the length of the napkin. The napkin is then placed onto this sheet with the longitudinal sides of the napkin essentially perpendicular to the short sides of the sheet, and preferably with the top major surface of the napkin (the surface normally worn against the body and without the adhesive element) facing the sheet. A first part of the sheet is then folded over the napkin about a line essentially coincidental to one longitudinal edge of the napkin so that this folded portion of the sheet forms a right triangular shape on the surface of the napkin. When, as in the preferred embodiment, the adhesive element is on the surface covered by this folded portion, the folded portion is advantageously adhered to and held in place by the adhesive element. Similarly, the remainder of the napkin is covered by folding a second portion of the sheet about a line coincidental with the second longitudinal edge of the napkin and again advantageously using the adhesive to hold this folded portion in place. In this manner, the napkin is fully covered using a minimum of sheet material. The hypotenuse of each of the triangular portions of the sheet each cross the adhesive element on the napkin at at least one point and, accordingly, it is assured that the sheet will be held in place by the adhesive element even though the sheet is not in perfect registration with the napkin.

Other closure means may be provided such as a cuff which folds over to seal the open end of the package. In still another embodiment, the sheet is formed integral with an envelope for receiving the wrapped napkin and further insuring that the used napkin is fully enclosed when disposing of the same.

BRIEF DESCRIPTION OF THE DRAWINGS

In the Drawings:

FIG. 1 is a perspective view of the wrapped, adhesively attached sanitary napkin of this invention, with parts broken away to expose internal features;

FIG. 2 is a cross-sectional view of the napkin of FIG. 1 taken through line 2—2;

FIG. 3 is an analogous cross-sectional view of a second embodiment of this invention;

FIG. 4 is a planar view of a napkin placed on a sheet prior to wrapping and illustrating another embodiment of this invention;

FIG. 5 is a planar view of the napkin and sheet of FIG. 4, in a partially folded condition;

FIG. 6 is a planar view of the napkin and sheet of FIGS. 4 and 5 in a completely wrapped condition;

FIG. 7 is a planar view of a wrapped napkin of this invention illustrating still another specific embodiment;

FIG. 8 is a cross-sectional view of the wrapped napkin of FIG. 7 taken along line 8—8;

FIG. 9 is a cross-sectional view of the wrapped napkin of FIG. 8 taken along line 9—9;

FIG. 10 is a perspective view of a used, wrapped and folded napkin prior to sealing and discarding;

FIG. 11 is a perspective view of the napkin of FIG. 10 after sealing;

FIG. 12 is a planar view of a napkin placed in a wrapper with an integral envelope and illustrating still another embodiment of this invention;

FIG. 13 is a cross-sectional view of the napkin and wrapper of FIG. 12 taken through line 13—13; and FIG. 14 is a perspective view of the napkin of FIG. 14, wrapped and being folded and placed in the envelope for discarding.

DETAILED DESCRIPTION OF THE INVENTION

FIGS. 1 and 2 illustrate an embodiment of the invention and specifically depict a wrapped sanitary napkin 10 with its bottom surface 12 facing upward in the drawing. The wrapped napkin comprises an absorbent core 14 which may be made up of any suitable absorbent material such as, for example, comminuted wood pulp fibers, cotton linters, rayon fibers, cottom staple, bleached sulfite creped wadding and the like. The core 14 is surrounded by a fluid pervious cover 16 which may be such sheet material as gauze or nonwoven fabrics reinforced with adhesive binders or the like. In certain instances, the portion of the cover overlying the bottom major surface of the napkin may comprise a fluid impermeable sheet material such as polyethylene or polypropylene, cellophane and other similar films. Such a napkin construction is described in U.S. Pat. No. 3,643,662, issued on Feb. 22, 1972 to M. McGuire.

Applied to the bottom surface of the napkin is a pressure sensitive adhesive element 18, which, in the configuration shown in FIG. 1, is in the form of a single band of pressure sensitive adhesive extending centrally and parallel to the longitudinal edges of the napkin. In use, the napkin is applied to the crotch portion of an undergarment by pressing the adhesive thereto and this may be worn, without substantial repositioning of the napkin, and without the need for belts, pins and the like as with conventional tabbed napkins. The adhesive element may comprise any of a large number of pressure sensitive adhesives now available on the market, including, for example, the so-called cold pressure sensitive adhesives such as the acrylate adhesives, e.g., vinyl acetate-2 ethyl hexyl acrylate copolymer which is generally combined with tackifiers such as, for example, ethylene amine. Alternatively, the adhesive may comprise the rapid setting thermoplastic (hot melt) adhesives such as block copolymers exemplified by styrene and butadiene styrene copolymers. The adhesive element may also comprise a two-sided adhesive tape such as that described in the aforementioned U.S. Pat. No. 3,643,662.

It will be understood that while a particular geometrical configuration for the adhesive element is illustrated, the advantages of this invention accrue to various patterns of adhesive elements such as squares, triangles or other forms as will occur to one skilled in the art.

In accordance with the teachings of this invention, means are provided for both protecting the adhesive element and the napkin prior to use. These means comprise a sheet 20 of flexible material, covering the top surface 22, the sides 24 and overlapping on the bottom surface 12. The sheet is then held in place by being adhered to the adhesive element and thus, the sheet and the adhesive element cooperate in that the sheet provides a protective covering for the adhesive whereas the adhesive provides a means for holding the sheet about the napkin to protect the napkin from soiling. By this simple expedient, it can be seen that the specially designed release strip heretofore found necessary for protecting the adhesive element in napkins of this type is completely eliminated while obtaining the advantages of a completely wrapped product. When using the napkin, the sheet may be simply pulled away from the adhesive element and folded up and placed in the user's purse. Thereafter, when discarding the used napkin, the sheet may be unfolded, the napkin placed onto the center of the sheet, the sheet refolded and adhered to the adhesive element, all these steps requiring only minimal handling of the used napkin itself. The fully wrapped napkin may now be discarded in a trash receptacle.

The embodiment shown in FIGS. 1 and 2 are so constructed as to provide a product which will not unintentionally unwrap even when handled by virtue of the fact that the longitudinal edge portions 26 of the covering sheet both contact and are adhered to the adhesive element. This configuration is relatively easy to achieve when wrapping a used napkin for discarding the same by simply taking care to register the napkin with respect to the unfolded sheet so that when the sheet is folded about the napkin, the edges adhere to the adhesive. A simple manual adjustment can be made should the registration be imperfect. In mass producing such wrapped napkins however, registration may become a problem, particularly when the adhesive element used is a narrow adhesive band. Accordingly, it may be more advantageous to produce a product wrapped as illustrated in FIG. 3. Depicted there is sanitary napkin 10, overwrapped by the flexible sheet 20, but unlike the construction shown in FIGS. 1 and 2, the longitudinal edges 26 of the sheet 20 overlap on the top major surface 22 of the napkin rather than on the bottom surface 12 on which the adhesive element 18 is disposed. As in the prior embodiment, the sheet is held to the napkin by the adhesive element and similarly protects the adhesive element and the product from soiling. However, it will be appreciated that in this embodiment, even gross misregistration of the sheet and napkin will still provide a completely protected adhesive element. The fact that the longitudinal edges of the sheet are not adhered presents no great disadvantage when it is considered that the unused napkins are packaged closely together and not handled until use. When the time comes to dispose of a used napkin however, the same sheet may be applied as is shown in FIG. 1 and 2 by the user so that a safely wrapped napkin can be deposited in a trash receptacle.

Illustrated in FIGS. 4–6 is still another embodiment of this invention which more elegantly solves the aforementioned problem of registration while still maintaining the advantages of this invention in providing a completely wrapped product and eliminating the need for a special protective strip for the adhesive element. Shown in these figures is a sanitary napkin 30 similar in construction to the napkin 10 shown in FIGS. 1–3 in that napkin 30 comprises an absorbent core (not visible) overwrapped in a fluid-pervious cover 32 and, having on the bottom surface of the napkin (facing upward in the drawing) two pressure sensitive adhesive elements 34. For illustrative purposes, the adhesive elements 34 are shown as two rectangles extending transversely across the napkin and located at either end of the napkin. It will be understood that this configuration is one of many possible configurations and, for example, is completely interchangeable with the adhesive configuration shown in FIGS. 1–3 while still obtaining the advantages of this invention.

The napkin 30 is placed on a flexible sheet 36 which is in the shape of a parallelogram having two short parallel sides 38, 39 and two longer parallel sides 40, 41. The dimensions of the sheet are chosen relative to the size of the napkin such that the shorter parallel sides 38, 39 are at least twice as long as the width W of the napkin and are spaced apart by a distance at least as long as the length L of the napkin. The napkin is placed on the sheet preferably with the top major surface of the napkin facing the sheet, and with the longitudinal edges of the napkin essentially perpendicular to the short sides of the sheet.

FIG. 5 illustrates the embodiment shown in FIG. 4 with the napkin partially wrapped. The sheet is first folded about a line essentially coincidental to one longitudinal edge 42 of the napkin, with a corner of the sheet c folded over a second corner d, thus forming a right triangle cover 46 on the bottom major surface of the napkin. The right triangle covers approximately half of this surface and is held in place by overlying and adhering to one adhesive element 34. Illustrated in FIG. 6 is the completely wrapped napkin which is obtained by folding the sheet about a line essentially coincidental with the second longitudinal edge 44 of the napkin, with the corner of the sheet a folded over the corner b. Thus, again, a right triangle cover 48 is formed on the bottom major surface of the napkin and covers the remaining half of this surface. Again, this portion of the cover is adhered to second adhesive element 34. It will be appreciated that because the hypotenuse of each of the right triangles lies diagonally across the face of the napkin, of necessity at least a portion of each triangle will contact and adhere to one of the adhesive elements. Accordingly, even gross misregistration of the napkin as placed onto the sheet will not result in the sheet being unadhered to the adhesive and so this particular embodiment may be advantageously used in the rapid mass production of wrapped product. As in the prior embodiment described herein, the sheet may be saved by the user and employed in rewrapping the used product when disposing of the napkin.

The wrapped product illustrated in FIGS. 1–3 and FIG. 6 may be completely enclosed within the sheet by sealing the marginal edges of the sheet which extend beyond the ends of the napkin using such methods known in the art as heat sealing or adhesive sealing. Generally, such sealing is unnecessary in packaging unused napkins in that they are adequately protected from soiling by the unsealed flexible wrapper. When disposing of the napkin, however, it may be desirable to more effectively seal the used napkin for sanitary reasons. This may readily be accomplished by providing resealable adhesive elements on the marginal portions of the wrapped sheet. Another highly effective method is illustrated in FIGS. 7–11. Illustrated in FIGS. 7–9 is the wrapped napkin, in essentially the form of the embodiment shown in FIG. 6 with the exception that, on the uppermost triangle 48 of the folded sheet, a pocket or cuff 50 has been provided. The cuff may consist of a rectangular sheet of the same material as the flexible sheet, overlying the portion of the triangle 48 nearest one end of the napkin. The cuff is formed by sealing the periphery of the rectangular sheet to the triangular portion leaving an open mouth 52 facing the center of the wrapped napkin. The sealing may be accomplished by adhesive or heat seals 53. Alternatively, the rectangular sheet may be integral with the flexible sheet 38 and then folded about line e-a (see FIGS. 4 and 5) and sealed along the longitudinal edges to form the cuff.

In any event, the cuff now provides a convenient and easy-to-use means for sealing a wrapped used napkin. As is illustrated in FIG. 10, a used napkin, first wrapped as described above, is folded in half. Fingers may then be inserted into the mouth of the cuff at one end of the folded napkin and, as is shown in FIG. 11, the cuff may then be turned inside out around the other end of the napkin, thus producing a neatly sealed package which may be safely discarded and which has been formed around the used napkin with minimal handling of the napkin.

FIGS. 12 through 14 illustrate still a further embodiment of the instant invention. A rectangular sheet 60 having a length *k* equal to at least the length of the napkin is divided into a central portion 64 and two lateral portions 62 and 63, each of the portions being at least as wide as the width W of a napkin 68. Integral with the sheet 60 and extending from the central portion 64 is a bottom panel 70 also of a width and length at least as large as that of the napkin. Overlying the bottom panel 70 is a top panel 72 generally of the same dimensions as the bottom panel and sealed to the bottom panel along the peripheral edges 75, 75′, 75″ of the panels but unsealed at the edge facing the sheet 60 so as to form an envelope with a mouth 74 opening from the direction of the sheet 60. As shown in this specific embodiment, a cuff 78 is provided on the outside surface of the top panel 72 near the mouth 74, the cuff having a mouth 80 opening in a direction opposite to mouth 74. In using this sheet and integral envelope, the napkin 68 is laid onto the central portion 64 of sheet 60, preferably with the adhesive element 69 facing upwardly. Portions 62 and 63 are alternately folded or wrapped about the napkin. In this connection, it has been found desirable to provide slits 82 and 83 cut through the sheet 60 at the points where the sheet is integral with the formed envelope to facilitate the folding.

As is best illustrated in FIG. 14, the wrapped napkin may now be folded in half and rolled into the integral envelope. Thereafter, fingers may be inserted into the cuff at mouth 80 and the cuff turned about the open mouth 74 of the envelope to safely seal the napkin therein for discarding.

What is claimed is:
1. In a sanitary napkin having an adhesive element thereon for attaching to an undergarment, the improvement which comprises means for protecting said napkin and said adhesive element prior to use and for discarding said napkin after use, said means comprising a sheet of flexible wrapper material overlying one major surface and the sides of said napkin and at least partially overlapping on the second major surface of said napkin, said sheet being releasably adhered to and held in place by said adhesive element.

2. The improved sanitary napkin of claim 1 wherein said sheet overlaps on the major surface of the napkin on which the adhesive element is disposed.

3. The improvement of claim 2 wherein said sheet is in the form of a parallelogram having short parallel sides and long parallel sides, said short parallel sides being at least twice as long as the width of the napkin, and said short sides being spaced apart a distance at least as long as the length of said napkin.

4. The napkin of claim 1 wherein said flexible sheet is sealed to itself at one end of said napkin.

5. The napkin of claim 1 wherein a cuff is provided on the flexible sheet approximately one end of the napkin whereby said cuff may be turned around said end of the napkin to seal the napkin within the sheet.

6. The napkin of claim 1 wherein said sheet is integral with an envelope for receiving said napkin.

7. The napkin of claim 6 wherein said envelope is provided with a cuff at one end thereof whereby said napkin may be placed in said envelope and said cuff may be turned around said catamenial napkin to seal said napkin in said envelope.

* * * * *